(12) United States Patent
Blotsky et al.

(10) Patent No.: US 10,034,904 B2
(45) Date of Patent: *Jul. 31, 2018

(54) METHODS AND COMPOSITIONS OF BIOCONTROL OF PLANT PATHOGENS

(71) Applicant: CORE INTELLECTUAL PROPERTIES HOLDINGS, LLC, Goodyear, AZ (US)

(72) Inventors: Luke C. Blotsky, Goodyear, AZ (US); Derex Q. Zellars, Goodyear, AZ (US); Michael L. Lindsey, Goodyear, AZ (US)

(73) Assignee: Core Intellectual Properties Holdings, LLC, Goodyear, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/661,708

(22) Filed: Jul. 27, 2017

(65) Prior Publication Data

US 2017/0319635 A1 Nov. 9, 2017

Related U.S. Application Data

(63) Continuation of application No. 13/954,506, filed on Jul. 30, 2013, now Pat. No. 9,737,572.

(60) Provisional application No. 61/677,371, filed on Jul. 30, 2012.

(51) Int. Cl.
| | |
|---|---|
| *A01N 63/00* | (2006.01) |
| *A61K 35/74* | (2015.01) |
| *C12N 1/20* | (2006.01) |
| *C12R 1/07* | (2006.01) |
| *A61K 45/06* | (2006.01) |

(52) U.S. Cl.
CPC ............. *A61K 35/74* (2013.01); *A01N 63/00* (2013.01); *A61K 45/06* (2013.01); *C12N 1/20* (2013.01); *C12R 1/07* (2013.01)

(58) Field of Classification Search
CPC ...................................................... A01N 63/00
See application file for complete search history.

(56) References Cited

U.S. PATENT DOCUMENTS

| | | |
|---|---|---|
| 3,617,215 A | 11/1971 | Sugahara |
| 4,533,459 A | 8/1985 | Dente |
| 4,904,627 A | 2/1990 | Bhattacharyya |
| 6,602,500 B1 | 8/2003 | Kharbanda |
| 6,896,883 B2 | 5/2005 | Bergstrom |
| 7,074,565 B2 | 7/2006 | Dunbar |
| 9,113,605 B2 | 8/2015 | Hastings |
| 2002/0069685 A1 | 6/2002 | Adam |
| 2003/0166256 A1* | 9/2003 | Zahn .................. A01N 63/02 435/252.4 |
| 2004/0258597 A1 | 12/2004 | Michalakos |

(Continued)

OTHER PUBLICATIONS

Issue Notification mailed Apr. 9, 2014 for U.S. Appl. No. 10/725,729, filed Dec. 2, 2003 (Inventors—Blotsky et al.) (1 page).

(Continued)

*Primary Examiner* — Rosanne Kosson
(74) *Attorney, Agent, or Firm* — The Noblitt Group, PLLC

(57) ABSTRACT

The present invention comprises methods and composition for control of plant pathogens. Isolated bacteria, deposited with ATCC under the Budapest Treaty, are effective to control plant pathogens.

14 Claims, 3 Drawing Sheets

(56) References Cited

U.S. PATENT DOCUMENTS

2010/0092442 A1    4/2010   Jacobsen
2011/0253623 A1   10/2011   Hastings

OTHER PUBLICATIONS

Lee SJ, et al. (1998) Effects of harvesting method and growth stage on the flocculation of the green alga *Botryococcus braunii*. Letters Applied Microbiology. 27:14-18.
Metting B, et al. (1983) The Influence of a Microalgal Conditioner on Selected Washington Soils: An Empirical Study. Soil Sci. Soc. Am. J. 47:682-685.
Oh HM, et al. (2001) Harvesting of Chlorella vulgaris using a bioflocculant form *Paenibacillus* sp. AM49. Biotechnology Letters. 23:1229-1234.
Poelman E, et al. (1997) Potential of electrolytic flocculation for recovery of micro-algae. Resources, Conversation and Recycling. 19(1):1-10. (Abstract Only)
Suh HH, et al. (1998) Production and Rheological Properties of Biofloceulant Produced by *Bacillus* sp. DP-152. J. Microbiol. Biotechnol. 8(6):618-624.
U.S. Appl. No. 13/954,506, filed Jul. 30, 2013, Luke C. Blotsky
U.S. Appl. No. 61/677,371, filed Jul. 30, 2012, Luke C. Blotsky \* cited by examiner

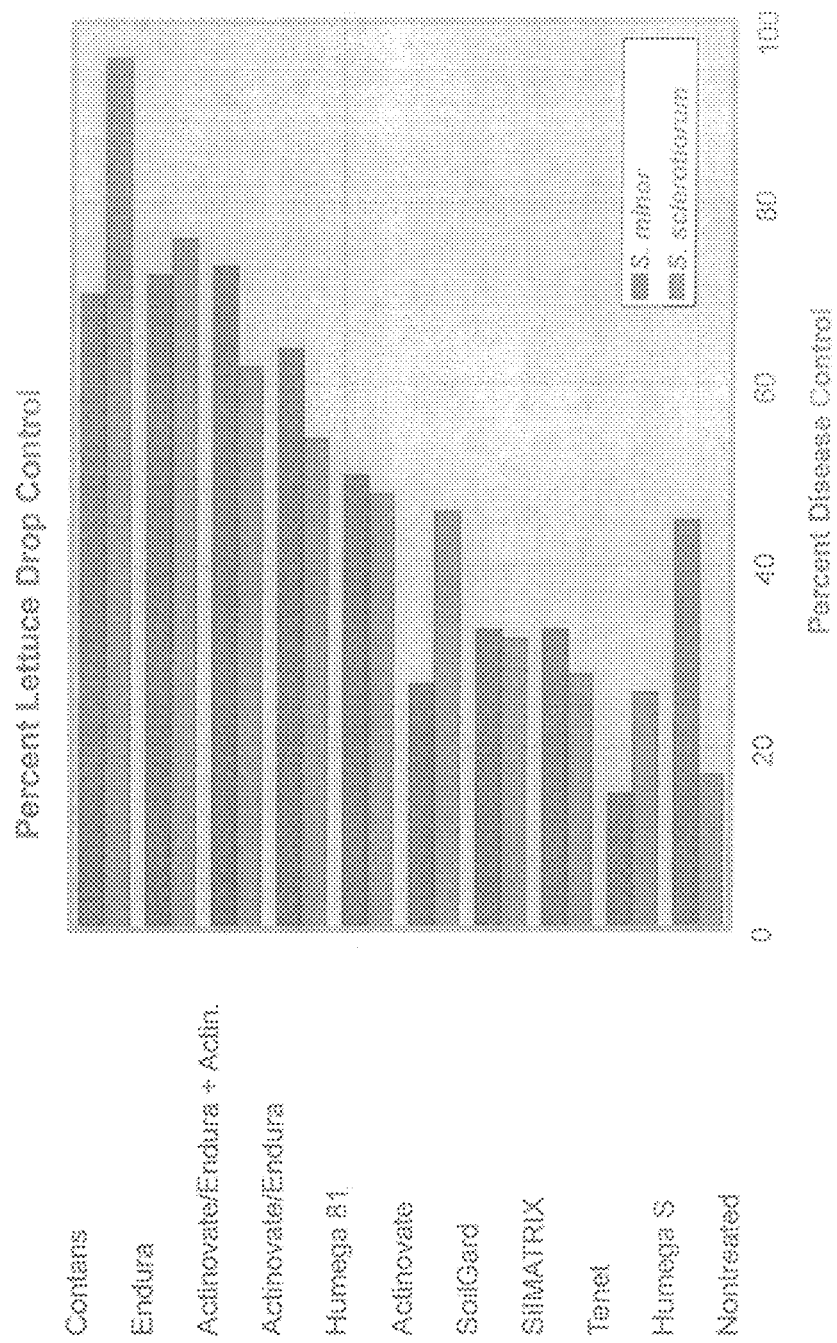

METHODS AND COMPOSITIONS OF BIOCONTROL OF PLANT PATHOGENS

RELATED APPLICATIONS

This application is a continuation of U.S. patent application Ser. No. 13/954,506, filed Jul. 30, 2013, which claims priority to and the benefit of U.S. Provisional Patent Application No. 61/677,371, filed Jul. 30, 2012, each of which is herein incorporated in its entirety.

TECHNICAL FIELD

The present invention relates to methods and compositions comprising isolated bacteria, particularly *Bacillus*, which are useful for biocontrol for plants.

BACKGROUND OF THE INVENTION

Application of chemical compounds to control plant pathogens has had quite a few adverse consequences for natural environments and human health. Biological control agents are desired to avoid or remediate these adverse effects. Biological control agents, such as microorganisms, may confer plant disease control by suppressing disease incidence and/or reducing the severity of symptoms caused by the pathogens.

Effective biological control of plant diseases with epiphytic microbes has been used with numerous phyllosphere- and rhizosphere-inhabiting organisms. Foliar biological control agents have included yeast and filamentous fungi, as well as bacteria; including gram negative species such as *Erwinia* sp. and *Pseudomonas* sp., and gram positive organisms such as *Bacillus* sp. It is thought that biological disease control is attributed to direct antagonism against the pathogen such as by production of antibiotics or hydrolytic enzymes or through competition for nutrients, though other mechanisms such as the induction of systemic resistance responses within the plant have also been attributed to biocontrol agents.

What is needed are compositions comprising biological control agents, such as bacteria, and methods for preventing and/or reducing plant disease by affecting plant pathogen activity and effect on the plants.

SUMMARY

The present invention comprises methods and compositions for treating plants, particularly compositions comprising isolated *Bacillus*, either as cells or spores or both, deposited with ATCC under the Budapest Treaty. The present invention comprises isolated *bacillus* organisms, referred to herein as biocontrol agents, and methods of using such biocontrol agents.

The present invention comprises isolated *bacillus* bacteria deposited with the ATCC under the Budapest Treaty and includes an isolated *Bacillus megaterium*, referred to by Applicants as isolate number 86, having ATCC Accession No. PTA-12845; an isolated *Paenibacillus polymyxa*, referred to by Applicants as isolate number 2, having ATCC Accession No. PTA-12841, an isolated *Bacillus vallismortis*, referred to by Applicants as isolate number 82, having ATCC Accession No. PTA-12844 an isolated *Bacillus subtilis spizizenii*, referred to by Applicants as isolate number 3, having ATCC Accession No. PTA-12842, and an isolated *Bacillus amyloliquefacians*, referred to by Applicants as isolate number 81, having ATCC Accession No. PTA-12843.

A biocontrol agent of the present invention, comprising one or more of the selected, isolated bacteria disclosed herein, is useful in methods of protecting plants against disease or damage by plant pathogens. A method comprises applying a biocontrol agent to plants, plant seeds, or media or soil surrounding plants under conditions effective provide disease protection to plants or plants produced from the contacted plant seeds.

The present invention comprises a method of enhancing plant growth. A method for enhancing plant growth comprises applying a biocontrol agent to plants, plants seeds, or media or soil surrounding plants under conditions effective to enhance growth in the plants or plants produced from the plant seeds.

Biocontrol agents of the present invention are useful in horticulture, aquaculture, aeroculture, hydroponic culture, agriculture and all types of plant growing conditions to protect plants from a variety of plant bacterial, fungal, and viral diseases. The compositions and methods of the present invention are effective against plant pathogens.

DESCRIPTION OF THE DRAWINGS

FIG. 3 is a graph showing the percent lettuce drop control for 11 treatments.

DETAILED DESCRIPTION

Figure 1:
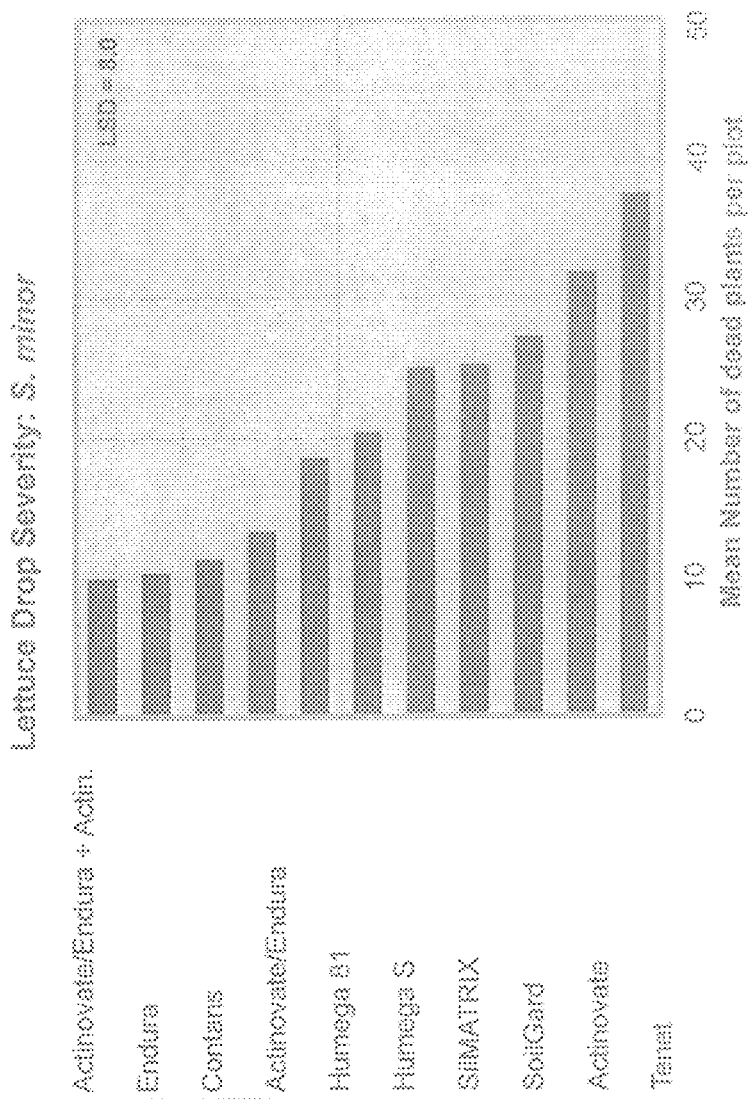
FIG. 1 is a graph showing the lettuce drop severity for *S. minor*.

The present invention comprises compositions comprising one or more isolated bacteria, deposited and disclosed herein, and methods of making and using such compositions. Compositions of the present invention comprise compositions comprising one or more of an isolated *Bacillus*, deposited under the Budapest Treaty and having ATCC Accession No. PTA-12845; having ATCC Accession No. PTA-12841; having ATCC Accession No. PTA-12844; having ATCC Accession No. PTA-12842; or having ATCC Accession No. PTA-12843, or combinations thereof. Methods of the present invention comprise isolating a bacteria from a source material, methods of using one or more isolated bacteria or compositions comprising one or more isolated bacteria, such as one or more *Bacillus* having Accession Nos. PTA-12845, PTA-12841, PTA-12844, PTA-12842, or PTA-12843. Methods of the present invention comprise modulating the effects of microorganisms on plants, seeds or plants grown from such seeds by contacting the plants, seeds or plants grown from contacted seeds with a biocontrol composition comprising one or more isolated bacteria, such as one or more *bacillus* organisms having Accession Nos. PTA-12845, PTA-12841, PTA-12844, PTA-12842, or PTA-12843.

The *Bacillus* and *Paenibacillus* strains disclosed herein were deposited with the American Type Culture Collection (ATCC), located at 10801 University Boulevard, Manassas, Va., 20110, USA, on Apr. 19, 2012.

Methods of the present invention comprise enhancing the growth of plants, seeds or plants grown from such seeds by contacting the plants, seeds or plants grown from contacted seeds with a composition comprising one or more isolated bacteria, such as one or more *Bacillus* having Accession Nos. PTA-12845, PTA-12841, PTA-12844, PTA-12842, or PTA-12843. One or more of the bacilli, in spore or non-spore form, having Accession Nos. PTA-12845, PTA-12841, PTA-12844, PTA-12842, or PTA-12843 is referred to herein as a biocontrol agent or agents, and a composition comprising one or more biocontrol agents is referred to as a biocontrol composition.

A biocontrol composition of the present invention comprises one or more isolated bacteria, such as one or more *Bacillus* having Accession Nos. PTA-12845, PTA-12841, PTA-12844, PTA-12842, or PTA-12843, wherein a biocontrol compositions comprises one or more of an isolated *Bacillus megaterium*, referred to by Applicants as isolate number 86, having ATCC Accession No. PTA-12845; an isolated *Paenibacillus polymyxa*, referred to by Applicants as isolate number 2, having ATCC Accession No. PTA-12841, an isolated *Bacillus vallismortis*, referred to by Applicants as isolate number 82, having ATCC Accession No. PTA-12844 an isolated *Bacillus subtilis spizizenii*, referred to by Applicants as isolate number 3, having ATCC Accession No. PTA-12842, and an isolated *Bacillus amyloliquefacians*, referred to by Applicants as isolate number 81, having ATCC Accession No. PTA-12843. A biocontrol composition comprising one or more isolated bacteria, such as one or more *Bacillus* having Accession Nos. PTA-12845, PTA-12841, PTA-12844, PTA-12842, or PTA-12843, may further comprise one or more carriers, such as an agricultural carrier which is known in the art. A carrier may be a solid particle, such as clay, to which a biocontrol composition is adhered. A carrier may be a liquid, and it is contemplated that the bacteria are not used with a strong acid or strong base. A biocontrol composition comprising one or more isolated bacteria, such as one or more *Bacillus* having Accession Nos. PTA-12845, PTA-12841, PTA-12844, PTA-12842, or PTA-12843, may further comprise biological or chemical compounds or agents. Biological or chemical compounds or agents may comprise a fertilizer, an insecticide, a fungicide, a nematocide, or mixtures thereof. A biocontrol composition comprising one or more isolated bacteria, such as one or more *Bacillus* having Accession Nos. PTA-12845, PTA-12841, PTA-12844, PTA-12842, or PTA-12843 may further comprise buffering agents, wetting agents, coating agents, abrading agents, clay, polysaccharides, or mixtures thereof. A biocontrol composition comprising one or more isolated bacteria, such as one or more *Bacillus* having Accession Nos. PTA-12845, PTA-12841, PTA-12844, PTA-12842, or PTA-12843 may be combined with water, irrigation water, nutrient media or other liquids to provide a liquid composition. A biocontrol composition comprising one or more isolated bacteria, such as one or more *Bacillus* having Accession Nos. PTA-12845, PTA-12841, PTA-12844, PTA-12842, or PTA-12843 may be combined with solids, such as soil, soil amendments, particles, potting soil, or other solids to provide a solid composition. A biocontrol composition comprising one or more isolated bacteria, such as one or more *Bacillus* having Accession Nos. PTA-12845, PTA-12841, PTA-12844, PTA-12842, or PTA-12843 may be encapsulated by, for example, polymeric materials including but not limited to polysaccharides, to provide an encapsulated formulation. Methods and compositions for encapsulating bacteria, for example, alginate compositions, are known in the art and are contemplated by the present invention. Encapsulated formulations of the present invention comprising a biocontrol composition comprising one or more isolated bacteria, such as one or more isolated *Bacillus* having Accession Nos. PTA-12845, PTA-12841, PTA-12844, PTA-12842, or PTA-12843 may be combined with liquids or solids and provided to plants by contacting plants, seeds or plants grown from such seeds by contacting the plants, seeds or plants grown from contacted seeds, or by contacting the soil, media, liquid or structures contacting the plants, plant parts, seeds and/or plants grown from contacted seeds. A biocontrol composition may be a liquid, solid, semi-solid or mixtures, admixtures, suspensions, or solutions thereof.

The present invention comprises an isolated *Bacillus megaterium*, referred to by Applicants as isolate number 86, having ATCC Accession No. PTA-12845; wherein *Bacillus megaterium* is rod-shaped gram positive endospore-forming species of bacteria. *Bacillus megaterium* is one of the largest eubacteria found in the soil and is able to survive in extreme conditions such as desert environments due to the spore it forms. *Bacillus megaterium* produces penicillin amylase used for making penicillin, and it is considered non-pathogenic saprophyte capable of recycling organic material in the soil. The prokaryotic cell is motile and is an aerobe.

The present invention comprises an isolated *Paenibacillus polymyxa*, referred to by Applicants as isolate number 2, having ATCC Accession No. PTA-12841, wherein *Paenibacillus polymyxa* is a gram-positive bacterium. *Paenibacillus polymyxa* vegetative state microorganisms are generally 1.8 to 2.2 µm in length and 0.6 to 0.8 µm in width. Colonies are mucous, slimy and tend to spread. *Paenibacillus polymyxa* bacteria generally aerobes and are capable of nitrogen fixation under anaerobic conditions. *Paenibacillus polymyxa* form biofilms in the rhizosphere around the root tips. This bacterium produces polymyxin lipopeptide against gram-negative bacteria. *Paenibacillus polymyxa* can withstand thermal resistance and are stable against acids as low as pH 2.0, and alkali high as pH 9.0. Endospores have longitudinal surfaces ridges. *Paenibacillus polymyxa* degrade pectin and plant polysaccharides. The bacterium *Paenibacillus polymyxa* is most effective in harsh and poor conditions.

The present invention comprises an isolated *Bacillus vallismortis*, referred to by Applicants as isolate number 82, having ATCC Accession No. PTA-12844. *Bacillus vallismortis* is a gram positive bacterium. *Bacillus vallismortis* vegetative cells are bacilli that are generally 0.8 to 1.0 µm wide and 2.0 to 4.0 µm long and occur singly and in short chains. *Bacillus vallismortis* cells are smooth and circular. The optimum growth temperature ranges from 28° C. to 30° C., with a maximum and minimum growth temperatures, respectfully, of 50° C. and 5 to 10° C. *Bacillus vallismortis* is motile, aerobic and growth occurs generally at a pH of 5.7. *Bacillus vallismortis* endospore released by the mother cell survives a heat survival screen at a concentration of a million cells per milliliter. Pigmentation can be observed after 4 days of incubation at 31° C.

The present invention comprises an isolated *Bacillus subtilis spizizenii*, referred to by Applicants as isolate number 3, having ATCC Accession No. PTA-12842, wherein *Bacillus subtilis* is a gram positive catalase positive bacterium commonly found in the soil. *Bacillus subtilis spizizenii* is rod shaped and has the ability to form a tough endospore allowing the bacterium to tolerate extreme environmental conditions. *Bacillus subtilis spizizenii* is an aerobe and is generally not considered a human pathogen nor is it toxigenic like some other members of the genus. *Bacillus subtilis spizizenii* is generally 1.1 µm to 1.5 µm wide and generally 2.0 µm to 6.0 µm long. This bacterium may be found living in dead organic matter. *Bacillus subtilis spizizenii* optimum growth temperatures are between 30° C. and 37° C. *Bacillus subtilis spizizenii* growth characteristic forms tan colors and slightly pigments. Growth of this bacterium occurs in a pH slightly neutral 6.5 to 7.0. The cell wall is rigid and composed of peptidoglycan polymers made mostly of sugars and amino acids. *Bacillus subtilis spizizenii* secretes enzymes amylase and protease.

The present invention comprises an isolated *Bacillus amyloliquefacians*, referred to by Applicants as isolate number 81, having ATCC Accession No. PTA-12843 wherein *Bacillus amyloliquefaciens* is a gram positive, catalase positive aerobic rod-shaped, motile bacteria. *Bacillus amyloliquefaciens* forms a strong endospore for use when conditions are not favorable and can be easily dispersed. *Bacillus amyloliquefaciens* ranges in size generally from 0.7 μm to 0.9 μm in width and generally 1.8 μm to 3.0 μm in length. *Bacillus amyloliquefaciens* optimal temperatures for growth are 30° C. to 40° C. Generally, no growth occurs below 15° C. and above 50° C. *Bacillus amyloliquefaciens* is an aerobe, however, in unfavorable conditions *Bacillus amyloliquefaciens* can survive and thrive in anaerobic environments. Active cells can reproduce within a pH range of 5.5 to 9.0. The strain produces liquefying amylase which is used in the hydrolysis of starch. The strain may also produce bacteriocins with bactericidal activity that inhibits the growth of pathogenic bacteria like *E. coli* and *Salmonella*.

The present invention comprises plants, plant parts, seeds and/or plants or plant parts from plants grown from contacted seeds that have been contacted by a biocontrol composition or an isolated biocontrol agent as described herein and at least a portion of the biocontrol composition or an isolated biocontrol agent is associated with the plant. Such plant parts have been contacted by a biocontrol composition or an isolated biocontrol agent as described herein and at least a portion of the biocontrol composition or an isolated biocontrol agent is associated with the plant part. Such seeds have been contacted by a biocontrol composition or an isolated biocontrol agent as described herein and at least a portion of the biocontrol composition or an isolated biocontrol agent is associated with the seeds. Plants grown from seeds contacted with a biocontrol composition or an isolated biocontrol agent as described herein or plant parts from such plants are also contemplated by the present invention, and such plants may or may not have at least a portion of a biocontrol composition or an isolated biocontrol agent as described herein associated with the plant.

A method for isolating a biocontrol agent comprises selecting for and isolating a bacterial isolate from a humic-containing soil, such as leonardite, or mixture of clay soils, or mixtures of clay soils and leonardite, as described in U.S. patent application Ser. No. 10/725,729, and related applications. Once a desirable naturally occurring soil or soil combination is obtained, the soil or soil combination is subjected to the extraction process described by U.S. patent application Ser. No. 10/725,729, which is herein incorporated in its entirety. Clay soils, mixtures of clay soils, or mixtures of clay soil(s) and leonardite are preferred in the practice of the invention. One reason such soil combinations are preferred is that such soils can be high in the mineral elements. A step in determining whether a clay soil or leonardite is acceptable as a source material is to determine the amount of arsenic, lead, mercury, and cadmium present in the source material soil, as little to no toxic elements are desired. Source material soil for composition of the present invention may or may not comprise one or all of the rare earth elements. For example, a lanthanum concentration of at least eighteen ppm and a scandium concentration of at least three and seven-tenths ppm may be found in a source material soil. Concentrations of promethium and gadolinium may also be found. Source material soil for composition of the present invention may or may not comprise at least ten rare earth elements, at least twelve, or more rare earth elements and optionally include lanthanum and scandium. Once leonardite or a clay soil or clay and leonardite combination is provided or is combined, the source material soil is subjected to the extraction process as taught by U.S. patent application Ser. No. 10/725,729.

In general, the extraction of the source material soil uses the following steps. Water, typically purified using known methods such as reverse osmosis, is added to citric acid and the source material soil in a mixing tank. The amount of citric acid (or of phosphoric acid or other edible acid(s)) or combinations thereof, may be in the range of 0.25% to 7.5% of the weight of water utilized, but typically is in the range of 1.0% to 2.0%. The water, citric acid and source material soil, form a slurry and the slurry is gently agitated (for example, with a blade slowly rotating at from one to ten RPM) for about an hour, although the agitation time can vary as desired. The slurry from the tank is directed into a settling tank to permit particulates to settle downwardly out of the slurry. The slurry is maintained in the settling tank for any desired length of time, in the range of about one to ten days. As the length of time that the slurry is maintained in the settling tank increases, the amount of liquid that can be drawn out of the tank and sent to a cooling tank or concentrator increases and the amount of solids that have settled to the bottom of the tank increases. Additives can be used to facilitate the settling of solids from slurry. After the slurry has resided in settling tank for the desired period of time, liquid is drawn out of the tank to a cooling tank, or directly to the concentrator. The solids on the bottom of tank are the material from which isolated bacteria of the present invention are isolated.

The solids are moist and spread on bacterial growth plates, such as nutrient media, PDA and other media known to those of skill in the art. Colonies were selected and a pure culture was obtained. The isolated bacteria were tested for activities such as production of enzymes, and antifungal properties, such as are known to those skilled in the art.

A biocontrol composition or an isolated biocontrol agent of the present invention is useful in methods of imparting to plants protection against plant pathogens. A method involves applying a biocontrol composition comprising one or more isolated bacteria, such as one or more bacteria having Accession Nos. PTA-12845, PTA-12841, PTA-12844, PTA-12842, or PTA-12843 or an isolated biocontrol agent comprising a bacteria having Accession Nos. PTA-12845, PTA-12841, PTA-12844, PTA-12842, or PTA-12843 to plants, plant parts, seeds and/or plants grown from contacted seeds, and/or or by contacting the soil, media, liquid or structures contacting the plants, plant parts, seeds and/or plants grown from contacted seeds, under conditions effective to impart disease protection to the plants, plant parts, seeds and/or plants grown from contacted seeds.

Methods of the present invention for imparting pathogen protection to plants may protect plants against infection or the effects of a wide variety of pathogens including viruses, bacteria, and fungi. For example, plants can be protected against infection by or effects from the growth of fungi including, but not limited to, *Fusarium oxysporum, Fusarium graminearum, Fusarium moniliforme, Cochliobolus sativus, Collectotrichum graminicola, Stagonospora nodorum, Stagonospora avenae, Stenocarpella maydis, Sclerotinia minor, Sclerotinia sclerotiorum, Sclerotinia* sp., *Pyrenophora tritici-repentis*, and other plant pathogenic fungi. For example, plants can be protected against infection by or effects from the growth of *Phytophthora*, a genus of plant-damaging Oomycetes (water molds). For example, plants can be protected against infection by or effects from the growth of bacterial plant pathogens on the plants or a systemic infection by bacterial plant pathogens. For example, plants can be protected against infection by or effects from the growth of viral plant pathogens on the plants or a systemic infection by viral plant pathogens. Pathogens of plants are known, and further examples of such pathogens are disclosed herein.

In methods of the present invention, plants, plant parts, seeds and/or plants grown from contacted seeds and/or media, soil or structures contacting the plants, plant parts, seeds and/or plants grown from contacted seeds are contacted with a biocontrol composition as disclosed herein. Contacting or applying methods may include, without limitation, applying compositions to soil or contacting one or more surfaces or portion(s) of a surface of a plant, plant part, seed and/or plant grown contacted seeds with a biocontrol composition comprising one or more isolated bacteria, such as one or more *Bacillus* having Accession Nos. PTA-12845, PTA-12841, PTA-12844, PTA-12842, or PTA-12843. The contacting or applying may be by any means, such as by spraying, sprinkling, irrigating, adding to water or other liquids provided to plants, adding as a solid, dry product, for example, by spreading, or tilling into the soil. Contacting may comprise painting or applying onto surfaces of structures that contact plants including but not limited to, pots, containers, shipping containers, storage containers, field instruments such as hoes, trowels, cutting implements, and/or shoes, gloves, and/or clothing worn by persons contacting plants.

A method of protecting plants against plant pathogens comprising, contacting plants, plant parts, seeds and/or plants grown from contacted seeds, media, soil or structures contacting the plants, plant parts, seeds and/or plants grown from contacted seeds with a composition comprising a biocontrol agent comprising one or more isolated *Bacillus* having Accession Nos. PTA-12845, PTA-12841, PTA-12844, PTA-12842, or PTA-12843 or a biocontrol agent comprising isolated *Bacillus* having Accession Nos. PTA-12845, PTA-12841, PTA-12844, PTA-12842, or PTA-12843, under conditions effective to protect the plants, plant parts, seeds and/or plants grown from contacted seeds against plant pathogens.

Conditions effective to protect the plants, plant parts, seeds and/or plants grown from contacted seeds include, but are not limited to, contacting at least one plant at one or more points in its growth cycle and providing an effective amount of a biocontrol composition or an isolated biocontrol agent as described herein to modulate, reduce, prevent, or ameliorate an infection by a plant pathogen. The contacting may occur one time at one point in the growth cycle, or may occur more than one time at one point in the growth cycle, or may occur one time at multiple points in the growth cycle, or may occur more than one time at more than one point in the growth cycle of a plant. A seed may be contacted such that at least a portion of a seed, such as a portion of the surface of the seed, is covered with an effective amount of a biocontrol composition or an isolated biocontrol agent as described herein. The biocontrol composition or isolated biocontrol agent may be adhered to all or a portion of the surface of a seed, for example, by allowing a liquid composition of a biocontrol composition or an isolated biocontrol agent as described herein to dry on the seed, or by pretreating the seed with agents that aid in adherence of the biocontrol composition or an isolated biocontrol agent as described herein. Such agents may include starches, glues, or other known compositions or molecules that aid in adherence. A biocontrol composition or an isolated biocontrol agent as described herein may be combined with agents that aid in adherence and then applied to a seed. As contemplated herein, seed includes, but is not limited to seeds, stalks, canes, nuts, fruits, tubers, and rhizomes. A biocontrol composition or isolated biocontrol agent may be adhered to all or a portion of the surface of a flower, for example, by allowing a liquid composition of a biocontrol composition or an isolated biocontrol agent as described herein to dry on the flower, or by pretreating the flower with agents that aid in adherence of the biocontrol composition or an isolated biocontrol agent as described herein.

Conditions effective to protect the plants, plant parts, seeds and/or plants grown from contacted seeds may comprise injection into plants, plant parts, seeds and/or plants grown from contacted seeds, injection into soil or media that surrounds or contacts the plants, plant parts, seeds and/or plants grown from contacted seeds, or application to the surface of soil or media that surrounds or contacts the plants, plant parts, seeds and/or plants grown from contacted seeds.

Methods disclosed herein may be used with plants, seeds, fruits or plant parts from a plant that is a food crop; a turf grass; a flowering plant, bush or tree; a fruit-bearing plant or vegetable; a household plant; a nursery plant; a landscape plant; a plant tissue culture, or a biomass plant. For example, the plant or seed contacted is a monocot or a dicot, including but not limited to alfalfa, rice, wheat, barley, rye, cotton, sunflower, peanut, corn, potato, sweet potato, bean, pea, chicory, lettuce, endive, cabbage, Brussel sprout, beet, parsnip, turnip, cauliflower, broccoli, turnip, radish, spinach, onion, garlic, eggplant, pepper, celery, carrot, squash, pumpkin, zucchini, cucumber, apple, banana, pear, melon, citrus, strawberry, grape, raspberry, pineapple, soybean, tobacco, tomato, sorghum, or sugarcane, ornamental plants, including but not limited to, *Arabidopsis thaliana, Saintpaulia, Petunia, Pelargonium, Euphorbia pulcherrima* (poinsettia), *Chrysanthemum, Dianthus caryophyllus* (carnation), and *Zinnia*.

A method of the present invention comprises enhancing plant growth by applying a biocontrol composition of the present invention to plants, plant seeds, and soil surrounding plants under conditions effective to enhance growth of the plants or plants resulting from the treated seeds. For example, when pathogens are reduced or eliminated, plant growth is enhanced. The enhancement of plant growth may begin from seeds or later in the life of a plant. For example, plant growth as used herein may comprise greater yield, increased quantity of seeds produced, increased percentage of seeds germinated, increased plant size, greater biomass, more and bigger fruit, earlier fruit coloration, and earlier fruit and plant maturation, and longer lasting production time by the plant. For example, early germination and early maturation permit crops to be grown in areas where short growing seasons would otherwise preclude their growth in that locale. Increased percentage of seed germination results in improved crop stands and more efficient seed use. Greater yield, increased size, and enhanced biomass production allow greater production from a given plot of land.

Methods of the present invention can be carried out through a variety of procedures when all or part of the plant is treated, including leaves, stems, roots, plant products (e.g., grain, fruit, forage, crop debris), propagules (e.g., cuttings), tissue cultures, cells, or other known plant parts or surfaces. Suitable application methods include high or low pressure spraying, drenching, and injection. For example, when treating plant seeds, in accordance with the present invention, a biocontrol composition or an isolated biocontrol agent as described herein can be applied by low or high pressure spraying, coating, immersion, or injection. A biocontrol composition or an isolated biocontrol agent as described herein may also be applied to pathogen-infested crop stubble in order to reduce the inoculum available to infect a subsequent crop, especially under conservation tillage agriculture. Other suitable application procedures can be envisioned by those skilled in the art. Once treated with a biocontrol composition or an isolated biocontrol agent as described herein, the seeds can be planted in natural or artificial soil and cultivated using conventional procedures to produce plants. After plants have been propagated from seeds treated in accordance with the present invention, the plants may be treated with one or more applications of a biocontrol composition or an isolated biocontrol agent as described herein to impart disease protection to plants and/or to enhance plant growth.

A biocontrol composition or an isolated biocontrol agent as described herein can be applied to plants or plant seeds in accordance with the present invention alone or in a mixture with other materials. Alternatively, the biocontrol agent can be applied separately to plants with other materials being applied at different times.

A composition suitable for treating plants or plant seeds in accordance with the present invention may comprise a carrier. Suitable carriers include water, aqueous solutions, slurries, solids (e.g., peat, wheat, bran, vermiculite, and pasteurized soil) or dry powders. In this embodiment, the composition contains $10_6$ to $10_8$ colony forming units of the biocontrol agent per milliliter of carrier. Compositions may comprise additives including fertilizer, insecticide, fungicide, nematacide, and mixtures thereof. Suitable fertilizers include $(NH_4)_2NO_3$. An example of a suitable insecticide is Malathion. Useful fungicides include Captan. Other additives may comprise buffering agents, wetting agents, coating agents, and abrading agents. These materials can be used to facilitate the process of the present invention. In addition, a biocontrol composition or an isolated biocontrol agent as described herein can be applied to plant seeds with other conventional seed formulation and treatment materials, including clays and polysaccharides.

The present invention comprises methods for contacting plants, plant parts, seeds and/or plants grown from contacted seeds, to modulate the effects of microorganisms, particularly pathogenic microorganisms, on the plants, plant parts, seeds and/or plants grown from contacted seeds. For example, the effects of one or more microorganisms may be reduced, eliminated or prevented by contacting plants, plant parts, seeds and/or plants grown from contacted seeds with a a biocontrol agent composition or an isolated biocontrol agent of the present invention. Plant disease may be said to be prevented when it is known that a field or other growing site or media is infested with one or more microorganisms that cause a pathological condition in a plant, and when a plant is grown in that field or site or media and the plant does not show the signs of infection by the microorganisms known to be present in the field, site or media, the plant disease is prevented. Studies with biocontrol compositions of the present invention have shown that after treatment with a biocontrol composition comprising at least one of the isolated bacteria biocontrol agents disclosed herein, the composition aids beneficial microorganisms that are present on the plants or in the soil. For example, after treatment with a biocontrol composition, pathogen microorganisms cannot be found, but there is an increased number of the biocontrol composition bacteria. Testing for microorganisms, such as testing for the presence of the *bacillus* microorganisms by heat survival test followed by selective media for *bacillus*, is found by sampling for bacteria under the soil surface and at the root zone, for example, 1-4 inches in the subsoil. Surface samples are too exposed and airborne spores are likely found.

In an embodiment, the plant is a monocot. For example, the monocot plant is in the gramineae and cereal groups. Non-limiting exemplary monocot species include grains, tropical fruits and flowers, banana, maize, rice, barley, duckweed, gladiolus, sugar cane, pineapples, dates, onions, pineapple, rice, sorghum, turfgrass and wheat. In another embodiment, the plant is a dicot. For example, the dicot plant is selected from the group consisting of Anacardiaceae (e.g., cashews, pistachios), Asteraceae (e.g., asters and all the other composite flowers), Brassicaceae (e.g., cabbage, turnip, and other mustards), Cactaceae (e.g., cacti), Cucurbitaceae (e.g., watermelon, squashes), Euphorbiaceae (e.g., cassaya (manioc)), Fabaceae (e.g., beans and all the other legumes), Fagaceae (e.g., oaks), Geraniales (e.g., Geranium), Juglandaceae (e.g., pecans), Linaceae (e.g., flax), Malvaceae (e.g., cotton), Oleaceae (e.g., olives, ashes, lilacs), Rosaceae (e.g., roses, apples, peaches, strawberries, almonds), Rubiaceae (e.g., coffee), Rutaceae (e.g., oranges and other citrus fruits), Solanaceae (e.g., potato, tomato, tobacco), Theaceae (e.g., tea), and Vitaceae (e.g., grapes).

An aspect of the present invention comprises microorganisms that affect plants, such as an infection of a plant wherein the infection is caused by any kind of infectious (i.e., biotic) agents that affect plants. Examples of such agents/pathogens include but are not limited to an agent or pathogen such as bacteria, fungi, and viruses. Examples of specific pathogens to be treated using the compositions and methods of the present invention include but are not limited to pathogens selected from the group consisting of *Mycosphaerella fijiensis* (Black sigatoka), *Cladosporium caryigenum* (pecan scab), *Glomerella cingulata* (Anthracnose), *Cercospora beticola* (*Cercospora* leaf spot), *Botrytis cinerea, Fusarium solani* f. sp. *cucurbitae* (*Fusarium* Crown rot), *Pseudomonas syringe* (angular leaf spot) and *Erwinia caratovora* (bacterial vascular necrosis).

Examples of bacteria that may cause infections treatable or preventable by compositions of the present invention include *Pseudomonas* species, particularly *Pseudomonas aeruginosa, Pseudomonas fluorecens*, and *Pseudomonas syringe* (angular necrosis), *Pantoua agglomorans, Erwinia tracheiphilia*, leaf spot). Other bacteria that may cause infections treatable or preventable by compositions of the present invention include *Erwinia* caratovora (bacterial vascular and *Zanthomonas axanopodis*. Depending on the species of bacteria and the tissue infected, the bacteria produce and release enzymes that degrade cell walls, growth regulators that alter the plants' normal growth, toxins that degrade cell membranes and/or complex sugars that plug water conducting tissue. A general classification of phytopathogenic prokaryotes are shown in Table 1.

TABLE 1

Kingdom: Procaryotae
Bacteria - Have cell membrane and cell wall and no nuclear membrane
Division: Bacteria - Gram-positive Class: Proteabacteria - Mostly single celled bacteria.

TABLE 1-continued

Family: Enterobacteriaceae Genus: *Erwinia*, causing fire blight of pear and apple, Stewart's wilt in corn, and soft rot of fleshy vegetables. *Pantoea*, causing wilt of corn. *Serratia*, *S. marcescens*, a phloem-inhabiting bacterium causing yellow vine disease of cucurbits. *Sphingomonas*, causing brown spot of yellow Spanish melon fruit.

Family: Pseudomonadaceae Genus: *Acidovorax*, causing leaf spots in corn, orchids and watermelon. *Pseudomonas*, causing numerous leaf spots, blights, vascular wilts, soft rots, cankers, and galls. *Ralstonia*, causing wilts of solanaceous crops. *Rhizobacter*, causing the bacterial gall of carrots. *Rhizomonas*, causing the corky root rot of lettuce. *Xanthomonas*, causing numerous leaf spots, fruit spots, blights of annual and perennial plants, vascular wilts and citrus canker. *Xylophilus*, causing the bacterial necrosis and canker of grapevines.

Family: Rhizobiaceae Genus: *Agrobacterium*, the cause of crown gall disease. *Rhizobium*, the cause of nitrogen- fixing root nodules in legumes.

Family: still unnamed Genus: *Xylella*, xylem-inhabiting, causing leaf scorch and dieback disease on trees and vines. *Candidatus liberobacter*, Phloem inhabiting, causing citrus greening disease. Unnamed, laticifer-inhabitingcausing bunchy top disease of papaya.

Division: Firmicutes - Gram-positive bacteria.

Class: Firmibacteria - Mostly single celled bacteria. Genus: *Bacillus*, causing rot of tubers, seeds, and seedlings and white stripe of wheat. *Clostridium*, causing rot of stored tubers and leaves and wetwood of elm and poplar.

Class: Thallobacteria - Branching bacteria. Genus: *Arthrobacter*, causing bacterial blight of holly, thought to be the cause of Douglas-fir bacterial gall. *Clavibacter*, causing bacterial wilts in alfalfa, potato, and tomato. *Curtobacterium*, causing wilt in beans and other plants. *Leifsonia*, causing ratoon stunting of sugarcane. *Rhodococcus*, causing fasciation of sweet pea. *Streptomyces*, causing common potato scab.

More plant pathogenic bacteria are described in Robert W. Jackson, Plant Pathogenic Bacteria: Genomics and Molecular Biology, published by Horizon Scientific Press, 2009, ISBN 1904455379, 9781904455370; Samuel S. Gnanamanickam, Plant-Associated Bacteria, published by Springer, 2007, ISBN 1402045379, 9781402045370; Martin Dworkin et al., The Prokaryotes: a handbook on the biology of bacteria, Published by Springer, 2006, ISBN 0387254927, 9780387254920; George N. Agrios, Plant pathology, published by Academic Press, 2005, ISBN 0120445654, 9780120445653; and David W. Parry, Plant pathology in agriculture, published by CUP Archive, 1990, ISBN 0521368901, 9780521368902.

Numerous classes of plant pathogenic fungi, including oomycetes, ascomycetes, and basidiomycetes, may cause infections treatable or preventable by compositions of the present invention in a plant. Examples of fungi that may cause infections treatable or preventable by compositions of the present invention in a plant include *Cercospora beticola* (*Cercospora* leaf spot), *Mycosphaerella fijiensis* (Black sigatoka), *Glomerella cingulate* (Anthracnose) and *Cladosporium caryigenum* (pecan scab). In general, fungal plant diseases can be classified into two types: those caused by soilborne fungi and those caused by airborne fungi, Soilborne fungi cause some of the most widespread and serious plant diseases, such as root and stem rot caused by *Fusarium* spp. and root rot caused by *Phytophthora* spp. For example, *Phytophthora parasitica* var. *nicotiana*, a soilborne oomycete found, in many tobacco growing regions worldwide, causes black shank, a highly destructive root and stem rot disease of many varieties of cultivated tobacco. Since airborne fungi can be spread long distances by wind, they can cause devastating losses, particularly in crops which are grown over large regions. A number of pathogens have caused widespread epidemics in a variety of crops. Diseases caused by airborne fungi are stem rust (*Puccinia graminis*) on wheat, corn smut (*Ustilago maydis*) on corn, and late blight disease (*Phytophthora infestans*) on potato and tomato. *Plasmopara viticola* is an airborne oomycete that causes downy mildew disease on grape vines. The blue mold fungus (*Peronospora tabacina*) has caused catastrophic losses in tobacco crops, particularly in the United States and Cuba. Most of these fungal diseases are difficult to combat, and farmers and growers must use a combination of practices, such as sanitary measures, resistant cultivars, and effective fungicide against such diseases. Billions of dollars are spent annually for chemical control of plant-pathogenic fungi. As a result, there is today a real need for new, more effective and safe means to control plant-pathogenic fungi, particularly oomycete, which are responsible for major crop loss. Oomycetes is a class of Oomycota, which is a phylum of filamentous protists, containing over around 70 genera and more than 800 known species (J. W. Deacon Modern mycology Edition: 3, Published by Wiley-Blackwell, 1997 ISBN 0632030771, 9780632030774).

"Oomycota" means "egg fungi", referring to the oversize oogonia which house the female gametes (eggs). Despite the name and their superficial appearance, oomycetes are not fungi. They are unicellular heterokonts, physically resembling fungi. Oomycetes are commonly known as water molds (or water moulds) or downy mildew. They are microscopic, absorptive organisms that reproduce both sexually and asexually and are called its thallus). Those skilled in the art understand the distinctions of oomycetes.

The *Phytophthora* group is a genus that causes diseases such as dieback, late blight in potatoes, sudden oak death, rhododendron root rot, and ink disease in the American Chestnut.

The *Pythium* group is even more prevalent than *Phytophthora* and individual species have larger host ranges, usually causing less damage. *Pythium* damping off is a very common problem in greenhouses where the organism kills newly emerged seedlings. Mycoparasitic members of this group (e.g. *P. oligandrum*) parasitize other oomycetes and fungi, and have been employed as biocontrol agents. One *Pythium* species, *Pythium insidiosum* is also known to infect mammals.

A third group of oomycetes is the downy mildews, which are easily identifiable by the appearance white "mildew" on leaf surfaces.

Oomycete-caused plant diseases include, but are not limited to, grape downy mildew (caused by *Plasmopara viticola*) and potato late blight (caused by *Phytophthora infestans*) and oomycete infestation of Arctotis (caused by *Bremia lactucae*), *Chenopodium murale* (caused by *Peronospora farinosa*), cucurbits and cucumbers (caused by *Pseudoperonospora cubensis*), grasses and grains (caused by *Sclerospora graminicola*), lettuce (caused by *Bremia lactucae*), onion (caused by *Peronospora destructor*), alfalfa (caused by *Peronospora trifoliorum*), lima bean (caused by *Phytophthora phaseoli*), sunflower (caused by *Plasmopara halstedii*), carrot (caused by *Plasmopara nivea*, also called *Plasmopara crustosa*), hops (caused by *Pseudoperonospora humuli*), crucifers (caused by *Peronospora parasitica*), spinach (caused by *Peronospora effusa*), beet (caused by *Peronospora schachtii*, also called *Peronospora farinosa*), peas (caused by *Peronospora viciae*), rose (caused by *Peronospora sparsa*), poppy (caused by *Peronospora arborescens*), tobacco (caused by *Peronospora hyoscami*), and violet (caused by *Peronospora violae*).

Plant viruses are affecting plants. Examples of viruses that may cause infections treatable or preventable by compositions of the present invention in a plant include cucumber mosaic, tobacco mosaic, and barley yellow dwarf virus. Plant viruses are obligate intracellular parasites that do not have the molecular machinery to replicate without a host. Those skilled in the art can recognize and identify diseases caused by plant viruses. Non-limiting exemplary plant viruses species are Alfalfa mosaic virus (Alfamovirus), Apple chlorotic leaf spot virus (Trichovirus), Apple scar skin viroid (Viroids), Arabis mosaic virus (Nepovirus), Barley mild mosaic virus (Bymovirus), Barley stripe mosaic virus (Hordeivirus), Barley yellow mosaic virus (Bymovirus), Bean common mosaic virus (Potyvirus), Bean yellow mosaic virus (Potyvirus), Beet necrotic yellow vein virus (Furovirus), Blackeye cowpea mosaic virus (Potyvirus), Bean common mosaic virus (Potyvirus), Broad bean wilt virus (Fabavirus), Butterbur mosaic virus (Carlavirus), Carnation mottle virus (Carmovirus), Carnation vein mottle virus (Potyvirus), Cauliflower mosaic virus (Caulimovirus), Chrysanthemum mild mottle virus (Cucumovirus), Tomato aspermy virus (Cucumovirus), Chrysanthemum stunt viroid (Viroids), Citrus mosaic virus, Citrus tristeza virus (Closterovirus), Clover yellow vein virus (Potyvirus), Cocksfoot mottle virus (Sobemovirus), Cucumber green mottle mosaic virus (Tobamovirus), Cucumber mosaic virus (Cucumovirus), Cycas necrotic stunt virus (Nepovirus), Dasheen mosaic virus (Potyvirus), Grapevine Algerian latent virus (Tombusvirus), Konjac mosaic virus (Potyvirus), Melon necrotic spot virus (Carmovirus), Mulberry ringspot virus (Nepovirus), Narcissus mosaic virus (Potexvirus), Plant viruses are viruses affecting plants. Examples of viruses that may cause Odontoglossum ringspot virus (Tobamovirus), Papaya ringspot virus (Potyvirus), Peach latent mosaic viroid, Peanut mottle virus (Potyvirus), Peanut stripe virus (Potyvirus), Bean common mosaic virus (Potyvirus), Peanut stunt virus (Cucumovirus), Potato virus A (Potyvirus), Potato virus M (Carlavirus), Potato virus S (Carlavirus), Potato virus X (Potexvirus), Potato virus Y (Potyvirus), Prune dwarf virus (Ilarvirus), Prunus necrotic ringspot virus (Ilarvirus), Radish mosaic virus (Comovirus), Rice black streaked dwarf virus (Fijivirus), Rice dwarf virus (Reovirus), Rice grassy stunt virus (Tenuivirus), Rice stripe virus (Tenuivirus), Rice tungro spherical virus (Sequivirus), Rice waika virus, Rice tungro spherical virus (Sequivirus), Ryegrass mottle virus, Satsuma dwarf virus (Nepovirus), Soil-borne wheat mosaic virus (Furovirus), Southern bean mosaic virus (Sobemovirus), Soybean mosaic virus (Potyvirus), Soybean stunt virus (Cucumovirus), Cucumber mosaic virus (Cucumovirus), Tobacco mosaic virus (Tobamovirus), Tobacco mosaic virus (Tobamovirus), Tomato mosaic virus (Tobamovirus), Tobacco necrosis virus (Necrovirus), Tobacco rattle virus (Tobravirus), Tobacco ringspot virus (Nepovirus), Tomato aspermy virus (Cucumovirus), Tomato black ring virus (Nepovirus), Tomato mosaic virus (Tobamovirus), Tomato ringspot virus (Nepovirus), Tomato spotted wilt virus (Tospovirus), Turnip mosaic virus (Potyvirus), Watermelon mosaic virus 1 (Potyvirus), Papaya ringspot virus (Potyvirus), Watermelon mosaic virus 2 (Potyvirus), Wheat yellow mosaic virus (Bymovirus), Zucchini yellow mosaic virus (Potyvirus). More plant viruses have been described in F. C. Bawden, Plant Viruses and Virus Diseases, Publisher Biotech Books, 2002, ISBN 8176220647, 9788176220644, which is incorporated herein by its entirety for all purposes.

Methods of the present invention may comprise contacting plants, plant parts, seeds and/or plants grown from contacted seeds, and/or a media, water, liquid, soil or other solid structure associated with the plants, plant parts, seeds and/or plants grown from contacted seeds. An aspect of the present invention comprises contacting or applying to the foliage of the plant a composition comprising a one or more isolated bacteria, such as one or more *Bacillus* having Accession Nos. PTA-12845, PTA-12841, PTA-12844, PTA-12842, or PTA-12843, or one or more isolated *Bacillus* having Accession Nos. PTA-12845, PTA-12841, PTA-12844, PTA-12842, or PTA-12843, for example for use as a biocontrol agent.

A biocontrol agent composition or an isolated biocontrol agent may be applied to the foliage of the plant by methods known in the art. For example, a biocontrol agent composition or an isolated biocontrol agent may be applied aerially. A biocontrol agent composition or an isolated biocontrol agent may be sprayed from above the plants, for example from an airplane. A concentration of a biocontrol agent composition or an isolated biocontrol agent applied aerially is $10^3$-$10^{12}$ cfu ("colony forming units")/ml, $10^4$-$10^{10}$ cfu/ml, $10^5$-$10^9$ cfu/ml, or $10^6$-$10^8$ cfu/ml. A biocontrol agent composition or an isolated biocontrol agent can be applied at a wide range of volume/acre of plants treated. For example, a biocontrol agent composition or an isolated biocontrol agent may be applied at 1-100 gallons/acre, 2-50 gallons/acre, 5-10 gallons/acre, 6-8 gallons/acre, or 2-10 gallons/acre.

A biocontrol agent composition or an isolated biocontrol agent can also be applied from the ground, for example by any agricultural spray equipment, including any sprayer, either manual or automatic, that can be used to apply a biocontrol agent composition or an isolated biocontrol agent to plants, plant parts, seeds and/or plants grown from contacted seeds, for example, the foliage of a plant. A concentration of a biocontrol agent composition or an isolated biocontrol agent applied from the ground is $10^3$-$10^{12}$ cfu ("colony forming units")/ml, $10^4$-$10^{10}$ cfu/ml, $10^5$-$10^9$ cfu/ml, or $10^6$-$10^8$ cfu/ml. A biocontrol agent composition or an isolated biocontrol agent can be applied from the ground at a wide range of volume/acre of plants treated. For example, a biocontrol agent composition or an isolated biocontrol agent may be applied at 10-500 gallons/acre, 10-100 gallons/acre, or 5-20 gallons/acre.

A biocontrol agent composition or an isolated biocontrol agent of the present invention may be applied to plants, plant parts, seeds and/or plants grown from contacted seeds as a spray-dried formulation suspended in an aqueous solution. An aspect of the present invention comprises a biocontrol agent composition or an isolated biocontrol agent comprising freshly grown cells. An aspect of the present invention comprises a biocontrol agent composition or an isolated biocontrol agent comprising spores of bacteria having Accession Nos. PTA-12845, PTA-12841, PTA-12844, PTA-12842, or PTA-12843. In an embodiment of the present invention, a biocontrol agent composition or an isolated biocontrol agent is formulated with a carrier to aid dilution and dispersion, and such a carrier may include various types of clay such as attaclay.

Methods and compositions of the present invention comprising a biocontrol agent composition or an isolated biocontrol agent may further comprise one or more additional biological or chemical agents, which may be included in a biocontrol agent composition or may comprise an isolated biocontrol agent, or may be applied to plants, plant parts, seeds and/or plants grown from contacted seeds prior to, or media, soil or structures contacting the plants, plant parts, seeds and/or plants grown from contacted seeds, simultaneously with, sequentially or after applications of one or more compositions of the present invention.

The present invention also provides methods of applying compositions of the present invention to a plant further comprising applying one or more biological or chemical compounds or control agents, referred to herein as a second control agent, which is not to be seen as limiting the composition or method to comprise only a second agent, but includes one or more control agents. In an embodiment, a second biological or chemical control agent is antibacterial, antifungal, antiviral, a plant activating agent, a pesticide, combinations of these or other known biological or chemical compounds or control agents used for plants and plant disease. The amounts used in making a composition comprising a biocontrol agent composition or an isolated biocontrol agent and a second control agent can be determined by those skilled in art who can use known quantities of each as are commonly applied, or can utilize test plots or tests known for determining quantities of applications to plants. Such experimentation is not undue and is within the skills of those in the plant industries.

Non limiting exemplary bactericides include, active chlorine (i.e., hypochlorites, chloramines, dichloroisocyanurate and trichloroisocyanurate, wet chlorine, chlorine dioxide etc.), active oxygen (peroxides, such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxy-ethanol and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants, such as some quaternary ammonium cations (such as benzalkonium chloride, cetyl trimethylammonium bromide or chloride, didecyldimethyl ammonium chloride, cetylpyridinium chloride, benzethonium chloride) and others, non-quaternary compounds, such as chlorhexidine, glucoprotamine, octenidine dihydrochloride etc.), strong oxidizers, such as ozone and permanganate solutions; heavy metals and their salts, such as colloidal silver, silver nitrate, mercury chloride, phenylmercury salts, copper sulfate, copper oxide-chloride etc.

Commonly used fungicides include, but are not limited to, benomyl, TPTH, propiconazole, tetraconazole, benimidazoles, triazoles, strobilurins, carboxamides, sulfananilides, phenylsulfamides, azoles, nitrogenous heterocycles, dicarboximides, phthalimides, carbamates, thiocarbamates, formaidines, antibiotics, aromatics, guanidines, organochlorine compounds, organometallics, organophosphorus compounds, nitrophenyl compounds, sulfur heterocyclyl compounds, ureas, inorganics, and others (e.g., benzamacril, carvone, essential oil extract from plants, cedar leaf oil, neem oil, chloropicrin, DBCP, drazoxolon, fenaminosulf, metzoxolon, oxolinic acid, spiroxamine, cymoxanil, metrafenone. Prohexadione calcium, thicyofen, dithane, chlorothalanil, dichlorophen, dicloran, nitrothal-isopropyl, bronopol, diphenylamine, mildiomycin, oxin-copper, cyflufenamide (e.g., N-(cyclopropylmethoxyimino-(6-difluoromethoxy-2,3-difluorophenyl)-methyl)-2-phenylacetamide), UK-2A (antibiotic isolated from *treptomyces* sp. 517-O.sub.2).

Plant activating agents are natural or synthetic substances that can stimulate, maintain, or enhance plant resistance to biotic and/or abiotic stressors/pressures, which include, but are not limited to, acibenzolar, probenazole, isotianil, salicyclic acid, azelaic acid, hymexazol, brassinolide, forchlorfenuron, benzothiadiazole (e.g., ACTIGARD® 50WG), microbes or elicitors derived from microbes, More plant activating agents are described in U.S. Pat. Nos. 6,849,576, 5,950,361, 6,884,759, 5,554,576, 6,100,092, 6,207,882, 6,355,860, 5,241,296, 6,369,296, 5,527,783, and 6,987,130. Microbes, or chemical compounds and peptides/proteins (e.g., elicitors) derived from microbes, can also be used as plant activating agents. Non-limiting exemplary elicitors are: branched-.beta.-glucans, chitin oligomers, pectolytic enzymes, elicitor activity independent from enzyme activity (e.g. endoxylanase, elicitins, PaNie), avr gene products (e.g. AVR4, AVR9), viral proteins (e.g. vial coat protein, Harpins), flagellin, protein or peptide toxin (e.g. victorin), glycoproteins, glycopeptide fragments of invertase, syringolids, Nod factors (lipochitooligo-saccharides), FACs (fatty acid amino acid conjugates), ergosterol, bacterial toxins (e.g. coronatine), and sphinganine analogue mycotoxins (e.g. fumonisin B1). More elicitors are described in Howe et al., Plant Immunity to Insect Herbivores, Annual Review of Plant Biology, 2008, vol. 59, pp. 41-66; Stergiopoulos, Fungal Effector Proteins Annual Review of Phytopathology, 2009, vol. 547, pp. 233-263; and Bent et al., Elicitors, Effectors, and R Genes: The New Paragigm and a Lifetime Supply of Questions, Annual Review of Plant Biology, 2007, vol. 45, pp. 399-436. Biological control agents are living organisms which can be used to eliminate or regulate the population of other living organisms. Biological control agents can be, for example, antibacterial agents, antifungal agents, antiviral agents, and insecticides. Examples of biological control agents include, but are not limited to, *Bacillus mycoides, Bacillus pumulis, Bacillus thuringiensis* (Bt), *Bacillus liquefacians*, numerous species of *Pseudomonas* bacteria, *Seratia marcesans*, and *Pantoua agglomerans*.

Chemical control agents are chemical substances which can be used to eliminate or regulate the population of living organisms. Chemical control agents can be, for example, antibacterial agents, antifungal agents, antiviral agents, and insecticides. Examples of chemical control agents include, but are not limited to, triphenyltin hydroxide (TPTH, Super-Tin, Griffin LLC), propiconazole (Tilt, Syngenta Crop Protection, Inc) and tetraconazole (Eminent, Sipcam Agro USA Inc.), benomyl, Strobilurin fungicides including Azoxystrobilurin (Syngenta), Trifloxstrobilurin (Bayer), Pyracstrobilurin (BASF) and Chlorthalonil fungicides.

In an aspect of the invention, a biocontrol agent composition or an isolated biocontrol agent is applied in conjunction with the application of a second biological or chemical control agent. A biocontrol agent composition or an isolated biocontrol agent may be mixed with the second biological or chemical agent and applied simultaneously to the plants, plant parts, seeds and/or plants grown from contacted seeds. A biocontrol agent composition or an isolated biocontrol agent and a second biological or chemical control agent may be applied separately but simultaneously to the plant. A biocontrol agent composition or an isolated biocontrol agent may be applied after the second biological or chemical control agent has been applied to the plants, plant parts, seeds and/or plants grown from contacted seeds, but during the time the biological or chemical control agent is acting as a control agent. A second biological or chemical control agent may be applied after the application of a biocontrol agent composition or an isolated biocontrol agent to plants, plant parts, seeds and/or plants grown from contacted seeds.

In an aspect, a biocontrol agent composition or an isolated biocontrol agent may be applied sequentially with a second biological or chemical control agent. For example, a biocontrol agent composition or an isolated biocontrol agent may be applied to the plants, plant parts, seeds and/or plants grown from contacted seeds. This sequential application may be repeated, as may other methods disclosed herein.

The present invention comprises plants, plant parts, seeds and/or plants grown from such seeds, that have been contacted by a biocontrol agent composition or an isolated biocontrol agent as described herein. Such plants, plant parts, seeds and/or plants grown from contacted seeds may be provided in methods that are normally used for providing plants, plant parts, seeds and/or plants grown from contacted seeds. For example, a nursery of young plants may be treated by contacting the plants' foliage, stems, stalks and/or roots with a biocontrol agent composition or an isolated biocontrol agent, allowing the composition to adhere to the contacted portion(s) of the plant, and then one or more contacted plants are provided to growers or other users of the young plants. Similar methods may be used for providing plant parts, seeds or plants grown from contacted seeds. A contacted seed is a seed that has been contacted by a biocontrol agent composition or an isolated biocontrol agent of the present invention.

It is an aspect of the invention to provide a plant to which a biocontrol agent has been applied. A plant to which a biocontrol agent has been applied is also referred to as a plant "treated" with a biocontrol agent. In an embodiment, the biocontrol agent is applied to the foliage of the plant. In an embodiment, the biocontrol agent is applied to the soil around the plant, or directly to the roots of the plant. In an embodiment, the phyllosphere of the plant is colonized by the biocontrol agent. In an embodiment the plant treated with a biocontrol agent is a banana, a curcubit, a pecan, a sugar beet, or a geranium.

Definitions

As used herein, the term "plant" refers to any living organism belonging to the kingdom Plantae (i.e., any genus/species in the Plant Kingdom). This includes familiar organisms such as but not limited to trees, herbs, bushes, grasses, vines, ferns, mosses and green algae. The term refers to both monocotyledonous plants, also called monocots, and dicotyledonous plants, also called dicots. Examples of particular plants include but are not limited to corn, potatoes, roses, apple trees, sunflowers, wheat, rice, bananas, tomatoes, opo, pumpkins, squash, lettuce, cabbage, oak trees, guzmania, geraniums, hibiscus, clematis, poinsettias, sugarcane, taro, duck weed, pine trees, Kentucky blue grass, zoysia, coconut trees, brassica leafy vegetables (e.g. broccoli, broccoli raab, Brussels sprouts, cabbage, Chinese cabbage (Bok Choy and Napa), cauliflower, cavalo, collards, kale, kohlrabi, mustard greens, rape greens, and other brassica leafy vegetable crops), bulb vegetables (e.g. garlic, leek, onion (dry bulb, green, and Welch), shallot, and other bulb vegetable crops), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of cucumis melons), water-melon, cantaloupe, and other cucurbit vegetable crops), fruiting vegetables (including eggplant, ground cherry, pepino, pepper, tomato, tomatillo, and other fruiting vegetable crops), grape, leafy vegetables (e.g. romaine), root/tuber and corm vegetables (e.g. potato), and tree nuts (almond, pecan, pistachio, and walnut), berries (e.g., tomatos, barberries, currants, elderberryies, gooseberries, honeysuckles, mayapples, nannyberries, Oregon-grapes, see-buckthorns, hackberries, bearberries, lingonberries, strawberries, sea grapes, lackberries, cloudberries, loganberries, raspberries, salmonberries, thimbleberries, and wineberries), cereal crops (e.g., corn, rice, wheat, barley, sorghum, millets, oats, ryes, triticales, buckwheats, fonio, and quinoa), pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fibber crops (e.g. hemp, cotton), ornamentals, and the like. For a more complete list of representative crop plants see, for example, Glossary of Crop Science Terms: III, Nomenclature, Common and Scientific Names, Crop Science Society of America, July 1992, which is herein incorporated in its entirety.

As used herein, the term "plant part" refers to a section or portion of a plant, whether a natural section, such as leaves, stalk, stem, trunk, root, rootlet, branch, branchlet, tuber, rhizome, or a portion such as one or more surfaces of a plant, a disc, cutting, rooted portion, leafed portion, plant protoplast, plant spore, plant shoot, plant tissue culture or plant tissue culture cells.

As used herein, the term "pesticide" refers to composition comprising one or more chemical substances or biological organisms capable of killing or inhibiting a pest. Pests include, but are not limited to, insects, pathogens (e.g., bacterium, fungi, viruses), weeds, molluscs, birds, mammals, fish, nematodes and microbes that compete with humans, e.g., for food. Pesticides can be classified into algicides, avicides, bactericides, fungicides, herbicides, insectcides, miticides/acaricides, molluscicides, nematicides, rodenticides, virucides, et al.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground"

part, also often referred to as the "roots". For a more comprehensive list of plant parts see, for example, James W. Perry and David Morton (1998) Photo Atlas for Botany, Wadsworth Publishing Company, 141 pages, which is herein incorporated in its entirety.

As used herein, the term "fungicide" refers to a composition comprising one or more chemical substances or biological organisms capable of killing or inhibiting both true fungi and their spores as well as oomycete pathogens, usually in a selective way. Fungicides are used both in agriculture and to fight fungal infections in animals. Fungicide can be either contact or systemic. In agriculture, a contact fungicide kills fungi by direct contact; a systemic fungicide spreads internally through the plant, thereby killing the fungia.

As used herein, the term "bactericide" refers to a composition comprising one or more chemical substances or biological organisms capable of killing or inhibiting bacteria, usually in a selective way.

EXAMPLES

Example 1: Method of Growing the Isolated Bacteria

Bacterial colonies were isolated from the solid material remaining after the extraction process performed on humic-containing soil, as described in U.S. patent application Ser. No. 10/725,729. Pure cultures were obtained by plating the isolated bacteria on nutrient agar or other selective agar. Bacterial isolates of the present were grown in sufficient numbers and are allowed to sporulate by reducing the nutrients in the media. The spores are stored. Spores were then admixed with compositions for treating plants.

Example 2: Method of Treating *Photophthora capsici* in Production of Jalapeno Peppers A trial to assess the protection of jalapeno peppers from phtoptera infection by application of a biocontrol composition of the present invention was conducted. The biocontrol composition comprised isolated bacteria having Accession Nos. PTA-12845, PTA-12841, PTA-12844, PTA-12842 and PTA-12843 at a concentration of $1\times10_6$ each, in a liquid organic fertilizer sold as Humega by Global Organics, Goodyear, Ariz. The trial was conducted as a strip designed trial using four single bed replications for each treatment, where the beds were 13.33 ft. wide by 150 feet in length. Each bed contained two lines of pepper plants. All applications were by a manifold attached to the in-field drip irrigation tape during a normal irrigation day. Treatments followed the rates and timing shown in the Treatment application Table shown below. The Grower Standard UTC was the control plot, which was not treated. The Ridomil Gold SL and Fungiphite were standard treatments used by growers and includes ridomil and a fungicide, Ridomil may be purchased from Novartis or Syngenta.

Full replicate counts of plants that were infected, dying or dead from *Photophthora capsici* were made at each evaluation. There were approximately 300 plants per replicate. Percent plant loss was based on the total number of plants infected or dying of date of analysis, divided by the total number of plants present on the day of panting, to equal a percent loss for that rating date. The plants were inspected for any application phototoxic effects after the initial application.

Average cumulative plant mortality due to *Photophthora capsici* was calculated. As can be seen, the biocontrol composition gave significant protection against *P. capsici* over the Control (untreated check) and the grower standard on most rating dates. By the end of the trial, the amount of mortality due to *P. capsici* for the biocontrol composition treated plants was almost half that seen in the Control (untreated check) and numerically much better than the grower standard program. No phytotoxic effects were seen in any of the treatments.

All data rated as significant was done using the New Duncan's Multiple Test Range at a 95% confidence level. It appears that the biocontrol composition provided superior reduction of death to pepper plants and protected against the effects of infection by *Photophthora capsici*.

TABLE 2

| # | Treatment | Rate | Application Description | Plant Mortality |
|---|---|---|---|---|
| 1 | Grower Standard UTC CONTROL | | | 16.1a |
| 2 | Ridomil Gold SL Fungiphite | 1 qt/A | 1 week post plant 3 weeks later | 13.2ab |
| 3 | Biocontrol composition comprising 5 *Bacillus*, having Accession Nos. PTA-12845, PTA-12841, PTA-12844, PTA-12842, and PTA-12843 | | 1 week post plant 3 weeks later | 9.5b |

Means followed by the same letter do not significantly differ. (P=0.05, Duncan's New MRT)

As the chart shows, a side by side comparison of growers standards, other fungicides compared to a biocontrol composition of the present invention comprising five isolates. The biocontrol compositions was effective against *Phytophthora capsici.*

Most fungicides currently used are not environmentally friendly and are very expensive. This study showed that the fungicides were not that effective against the pathogen, whereas the biocontrol composition was.

Example 3: Method of Treating *Sclerotinia* Drop on Lettuce

*Sclerotinia* disease develops when soil is wet and in temperatures from 10° C. to 25° C., optimally at 20° C. This disease is usually managed by destroying or inactivating the *sclerotinia* by fungicides, soil flooding and/or solarization.

This field trial was conducted on lettuce seeded on raised beds in double rows, 30 cm apart. At seeding, *sclerotinia* produced in the laboratory was spread on the surface of each 7.6 m long plot between the rows of lettuce seed and mixed into the top 5 cm of soil. There was 2100 spores/mL of *Sclerotinia* minor, 800 spores/mL of *S. sclerotiorum* per plot. Certain pathogens like *S. minor* and *S. sclerotiorum* produce spores. The test compositions were added at seeding applications. The field was irrigated by sprinkler irrigation to germinate seed, then furrow irrigated for remainder of trial. Subsequent applications of test compositions were at designated times. At crop maturity, the number dead plants per plot due to *Sclerotinia* infection was recorded.

TABLE 3

Test compositions

| Test Composition | Active Ingredient | Source | Applications |
|---|---|---|---|
| Actinovate | *Streptomyces lydicus* | Natural Industries | At seeding, after thinning |
| Contans | *Coniothyrium minitans* | SipcamAdvan | At seeding, after thinning |
| Endura | Boscalid | BASF | At seeding, after thinning |
| Biocontrol Comp1 | Isolated bacteria having Accession NoPTA-12844, | Inventors | At seeding, +14 and 28 days |
| Biocontrol Comp2 | Isolated bacteria having Accession No. PTA-12841 No. PTA-12844, PTA-12843. | Inventors | At seeding, +14 and 28 days |
| Sil-Matrix | Potassium silicate | Certix USA | At seeding, +6 times |
| SoilGard | *Gliocladium virens* | Certis USA | At seeding, after thinning |
| Tenet | *Trichoderma asperellum, T. gamsii* | SipcamAdvan | At seeding, after thinning |

Figure 2:
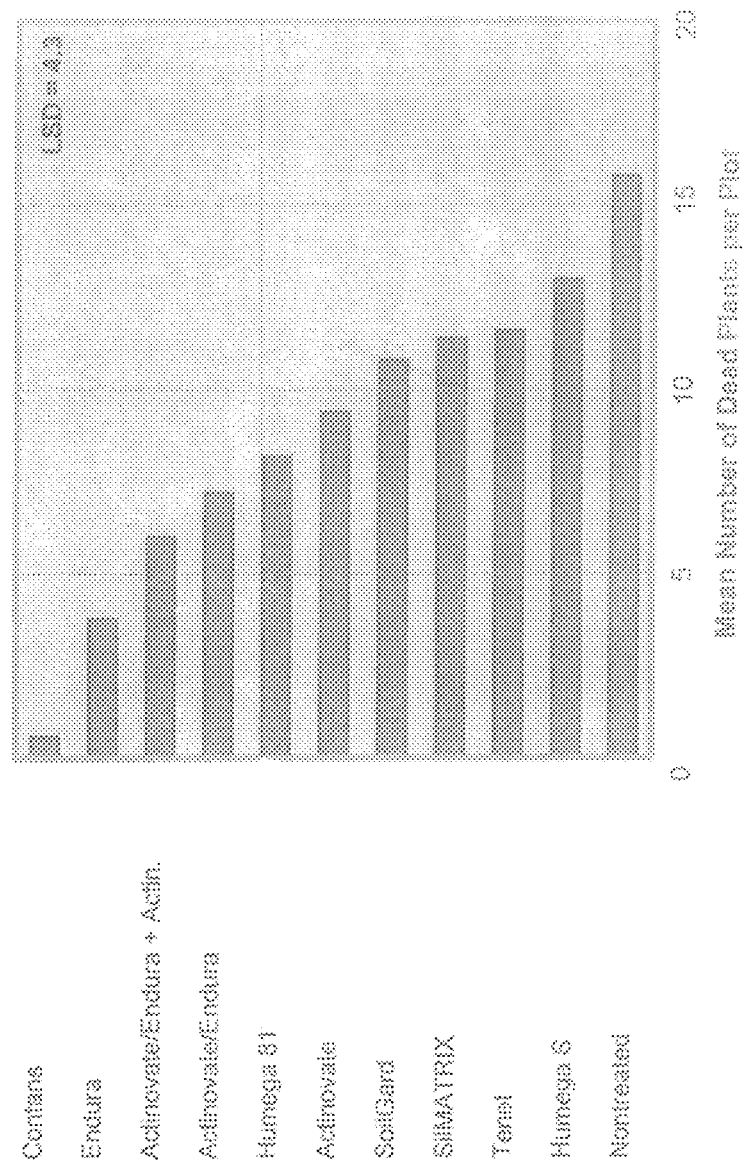
FIG. 2 is a graph showing the lettuce drop severity for *S. sclerotiorum*.

The lettuce drop severity for *S. minor* is shown in FIG. 1. Standard count was 50 plants per plot. The lettuce drop severity for *S. sclerotiorum* is shown in FIG. 2. Percent lettuce drop control is shown in FIG. 3. When compared to EPA registered products, biocontrol compositions of the present invention were cost effective for applications and yields. This test also showed that biocontrol compositions of the present invention was not disease specific in its effectiveness in reducing pathogens and aiding in plant growth. The other products used only treat this particular disease. Biocontrol compositions of the present invention have broad spectrum activity.

Example 4: Treatment of Onions

This test involved adding a biocontrol composition of the present invention (comprising isolated bacteria having Accession No. PTA-12845, No. PTA-12841, No. PTA-12844, No. PTA-12842, No. PTA-12843 at 1×10$_6$ spores/mL each, in a Humega liquid fertilizer, by Global Organics, Goodyear, Az), to a conventional fertilizer program for onions to reduce the incidence of *Scerotinia sclerotorium* infection in Red onion (*Allium cepa*). The Grower standard used their normal conventional fertilizer program.

A mixture of 2.5 gallons (10 liters was mixed with 25 gallons (100 liters) of water and applied to ¼ acrea at 20 days after transplant through a drenching program. Frequency of the applications were every two weeks for four applications.

The total number of plants tested was 25,000 plants. The control area had a percent of infestation of *S. sclerotorium* of over 70% in the control field. The treated field had an infestation of *S. sclerotorium* of 0.008%. The treated onions showed less damage than the untreated onions.

What is claimed is:

1. A method of treating plant soil or media to reduce plant pathogens, comprising, contacting plant soil or media with an effective amount of a composition comprising a carrier, an additive and a biocontrol composition, wherein the biocontrol composition consists of *Bacillus megaterium*, having ATCC Accession No. PTA-12845; *Paenibacillus polymyxa*, having ATCC Accession No. PTA-12841; *Bacillus vallismortis*, having ATCC Accession No. PTA-12844; *Bacillus subtilis spizizenii*, having ATCC Accession No. PTA-12842; and *Bacillus amyloliquefaciens*, having ATCC Accession No. PTA-12843, to reduce the effects of plant pathogens on a plant or seed grown in the plant soil or media.

2. The method of claim 1, wherein the composition further comprises a fertilizer, insecticide, fungicide, nematicide, or mixtures thereof.

3. The method of claim 1, wherein the composition further comprises buffering agents, wetting agents, coating agents, abrading agents, clay, polysaccharides, or mixtures thereof.

4. The method of claim 1, wherein the contacting is by topical application.

5. The method of claim 1, further comprising adding the biocontrol composition or one or more of the biocontrol agents to water provided to the plant soil or media.

6. The method of claim 1, wherein the plant or seed grown in the plant soil or media is a food crop; a turf grass; a flowering plant, bush or tree; a fruit-bearing plant or vegetable; a household plant; a nursery plant; a landscape plant; or a biomass plant.

7. The method of claim 1, wherein the plant or seed grown in the plant soil or media is alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, banana, pear, melon, citrus, strawberry, grape, raspberry, pineapple, soybean, tobacco, tomato, sorghum, or sugarcane.

8. A method of treating plant soil or media to reduce plant pathogens, comprising, contacting plant soil or media with an effective amount of a composition comprising a carrier, an additive and a biocontrol composition, wherein the biocontrol composition consists of *Paenibacillus polymyxa*, having ATCC Accession No. PTA-12841; *Bacillus vallismortis*, having ATCC Accession No. PTA-12844; and *Bacillus amyloliquefaciens*, having ATCC Accession No. PTA-12843, to reduce the effects of plant pathogens on a plant or seed grown in the plant soil or media.

9. The method of claim 8, wherein the composition further comprises a fertilizer, insecticide, fungicide, nematicide, or mixtures thereof.

10. The method of claim 8, wherein the composition further comprises buffering agents, wetting agents, coating agents, abrading agents, clay, polysaccharides, or mixtures thereof.

11. The method of claim 8, wherein the contacting is by topical application.

12. The method of claim 8, further comprising adding the biocontrol composition or one or more of the biocontrol agents to water provided to the plant soil or media.

13. The method of claim 8, wherein the plant or seed grown in the plant soil or media is a food crop; a turf grass; a flowering plant, bush or tree; a fruit-bearing plant or vegetable; a household plant; a nursery plant; a landscape plant; or a biomass plant.

14. The method of claim 8, wherein the plant or seed grown in the plant soil or media is alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, banana, pear, melon, citrus, strawberry, grape, raspberry, pineapple, soybean, tobacco, tomato, sorghum, or sugarcane.

* * * * *